United States Patent [19]
Perricaudet et al.

[11] Patent Number: 6,099,831
[45] Date of Patent: Aug. 8, 2000

[54] VIRAL RECOMBINANT VECTORS FOR EXPRESSION IN MUSCLE CELLS

[75] Inventors: Michel Perricaudet, Ouarville; Pascale Briand, Paris; Leslie Stratford-Perricaudet, Ouarville, all of France

[73] Assignee: Centre National de la Recherche Scientifique, Paris, France

[21] Appl. No.: 08/452,643

[22] PCT Filed: Sep. 25, 1992

[86] PCT No.: PCT/FR92/00898

§ 371 Date: Oct. 4, 1993

§ 102(e) Date: Oct. 4, 1993

[87] PCT Pub. No.: WO93/06223

PCT Pub. Date: Apr. 1, 1993

Related U.S. Application Data

[63] Continuation of application No. 08/070,325, filed as application No. PCT/FR92/00898, Sep. 25, 1992, abandoned.

[51] Int. Cl.$^7$ .................................................. A61K 48/00
[52] U.S. Cl. ...................... 424/93.2; 424/93.6; 435/320.1
[58] Field of Search ................................ 435/69.1, 172.1, 435/172.3, 320.1, 455, 456; 424/93.1, 93.2, 93.6

[56] References Cited

FOREIGN PATENT DOCUMENTS

| | | |
|---|---|---|
| 0 185 573 A1 | 11/1985 | European Pat. Off. . |
| WO 91/11525 | 1/1990 | WIPO . |
| WO 90/11092 | 10/1990 | WIPO . |
| WO 90/13640 | 11/1990 | WIPO . |
| WO 93/19191 | 9/1993 | WIPO . |

OTHER PUBLICATIONS

Dictionnaire Des Medicaments Veterinares, pp. 97, 98, 129, 130; 3rd Edition 1984 (Non Certified Translation).
Rosenfeld et al., Science 252: 431–434 (Apr. 19, 1991).
Verma et al., Nature, vol. 389, pp. 239–242, Sep. 18, 1997.
W. French Anderson, Nature, vol. 392, pp. 25–30, Apr. 30, 1989.
Orkin et al., "Report and Recommendations of the Panel to Assess the NIH Investment in Research on Gene Therapy", Dec. 7, 1995.
Marshall, "Gene Therapy's Growing Pains", Science, vol. 269, Aug. 25, 1995, pp. 1050–1055.
Morgan et al., "Human Gene Therapy", Ann. Rev. Biochem, 1993, vol. 62, pp. 191–217.
Quantin et al., "Adenovirus as an Expression Vector in Muscle Cells. Application to Dystrophen", Human Gene Transfer, vol. 219, pp. 271–272, Apr. 1991.
Stratford–Perricaudet et al. "Gene Transfer into Animals: The Promise of Adenovirus", Human Gene Transfer, vol. 219, pp. 51–61, Apr. 1991.

Primary Examiner—David Guzo
Attorney, Agent, or Firm—Merchant & Gould P.C.

[57] ABSTRACT

Non-replicatable viral recombinant vectors which are recognizable by muscle cell receptors, and furthermore modified by an insertion nucleic acid coding for a polypeptide sequence to be expressed in said muscle cells, are used to obtain a drug for treating muscle cell diseases or diseases which, by virtue of their location in the body, are accessible to the products of the expression of the above-mentioned nucleotide sequence, as secreted by said muscle cells. A method for producing said vectors, vectors such as those described above, and their use in pharmaceutical compositions are also provided.

6 Claims, 1 Drawing Sheet

FEUILLE DE REMPLACEMENT

VIRAL RECOMBINANT VECTORS FOR EXPRESSION IN MUSCLE CELLS

The present application is a continuation of U.S. Ser. No. 08/070,325, filed Oct. 4, 1993, now abandoned, which is the national phase application of PCT Application PCT/FR92/00898, filed Sep. 25, 1992.

The invention relates to recombinant vectors of viral origin which contain a nucleotide sequence coding for a specific polypeptide, and their use for the expression of this polypeptide in muscle cells. The invention also relates to a procedure for producing these vectors, as well as to their uses, in particular as medicines in the field of muscle diseases.

The hitherto unresolved problem of the direct diffusion of a gene towards a specific tissue is an obstacle to the development of gene therapy in the field of muscle diseases.

The various attempts to modify muscle tissue performed hitherto consist mainly of that involving fusion of muscle cells with a host cell (Salminen, A. et al., Hum. Gene Ther. 2, 15–26 (1991); Partridge, T. A. et al., Nature 337, 176–179 (1989), and that involving direct injection of DNA into the muscles (Wolff, J. A. et al., Science 247, 1465–1468 (1991); Acsadi, G., New Biol. 3, 71–81 (1991)).

The method proceeding by the fusion in mice of precursors of muscle cells derived from a normal donor with muscle fibers of a host (Partridge, T. A. et al., mentioned above) has been carried out with success and this cellular therapy has been the subject of preliminary trials in children. However, this approach seems to present too many disadvantages to be applicable to the treatment of muscle diseases. In fact, since the migratory capacities of the precursor cells are reduced to a few millimeters, the cellular implantation of these latter would necessitate millions of injections requiring hours of anaesthesia. Inevitably, there would be the risk of immunological problems leading to rejection phenomena occurring, as in the case of very many grafts. In addition, the treatment of Duchenne's muscular dystrophy (DMD) not only requires making contact with the skeletal muscles but also with the myocardial cells; the difficulties likely to be encountered in implanting precursors of muscle cells in the myocardium can easily be imagined. Consequently, cellular therapy hardly seems to be appropriate for the treatment of diseased cells showing such dissemination in the organism.

Gene therapy by direct in vivo introduction of nucleic acids into the interior of organs is an attractive method on account of its simplicity, but its development is confronted with a number of obstacles. In particular, the expression of genes in the muscles remains localised at the site of injection (Wolff, J. A. et al., mentioned above) and seems to be of quite limited duration, particularly in cardiac muscle (Acsadi, G. et al., mentioned above).

The aim of the present invention is precisely to make possible the introduction of a very large number of nucleic acids into a considerable number of muscle cells (up to 50% or more) of a human or animal organism, whether these muscle cells be those of skeletal muscle or those of the myocardium.

The present invention relates more particularly to the transport of nucleic acids to target muscle cells by the blood, while protecting these nucleic acids against attack by various blood constituents.

Another aim of the present invention is to make available to the public pharmaceutical compositions which make possible the treatment of muscle diseases, and more particularly genetic diseases of the muscle system, or also diseases, the localization of which in the organism makes them accessible to the expression products of the above-mentioned nucleic acids, these products being secreted by the said muscle cells.

The present invention follows from the discovery made by the inventors of the fact that beta-galactosidase activity is found in many tissues after injection into mice of recombinant vectors of viral origin, more particularly of adenoviral origin, into the genome of which the gene coding for beta-galactosidase has been inserted. Such tissues include the lungs, liver, intestine, heart and the skeletal muscles. The expression of the gene for beta-galactosidase is constant with time, since the proportion of blue-coloured cells (colour obtained subsequent to gene expression) in the muscle tissue is more or less the same from one month to the next.

Figure 1:
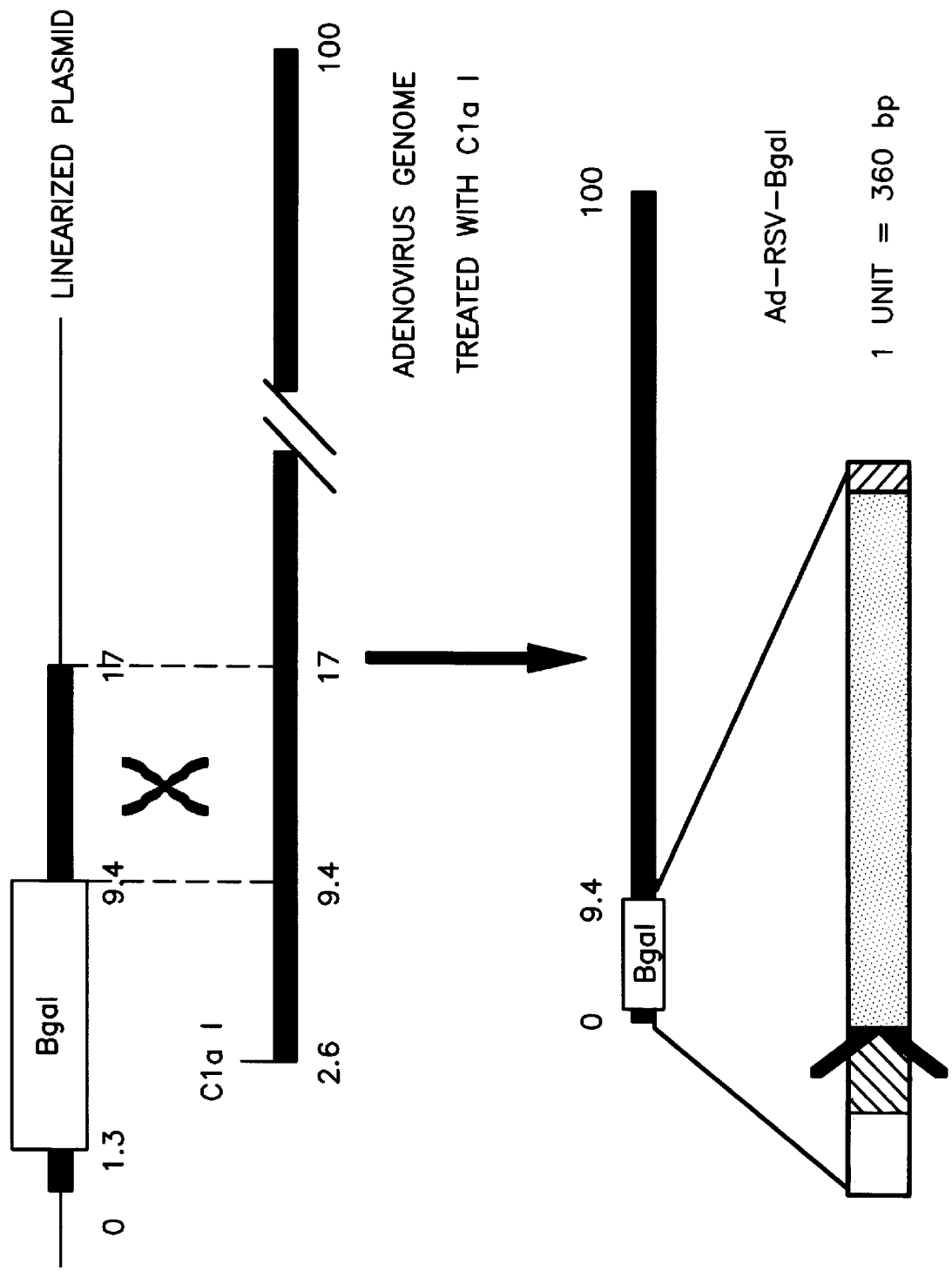
FIG. 1 shows an example of the construction of a recombinant vector according to the invention and corresponding to a type AdS adenovirus, into the genome of which the gene for beta-galactosidase has been inserted under the control of the RSV promoter.

The subject of the present invention is the use of recombinant vectors of viral origin, incapable of replication and likely to be recognized by the receptors of human and animal muscle cell which can be infected by these viruses, these vectors being additionally modified by a nucleic acid insert containing a nucleotide sequence which codes for a polypeptide sequence, the expression of which in the said muscle cells is sought, this sequence being under the control of a promoter recognized by the polymerases of these cells, for the production of drug compositions which can be administered by the general route, particularly the intravenous or intraarterial route, and designed for the treatment of either diseases affecting muscle cells or diseases, the localization of which in the organism makes them accessible to the expression products of the above-mentioned nucleic acids and secreted by the said muscle cells.

The adenoviruses, in particular the human adenoviruses type 2 or 5 represent particularly preferred vectors in the framework of the present invention by virtue in particularly of the large size of the foreign DNA fragment which it is possible to insert into the genome of these viruses.

Advantageously, the above-mentioned nucleic acid insert is included in a defective genome of an adenovirus, this genome lacking essential sequences necessary for the replication of these adenoviruses, and more particularly the EA and EB transactivators; nonetheless, this genome preferentially includes all of those essential sequences necessary for the encapsidation of these adenoviruses.

The promoter used may be an endogenous promoter (for example, an early or late promoter of the adenovirus used) or an exogenous promoter.

It will be advantageous to have recourse to strong promoters, for example one having about the same strength as the promoter contained in the LTR (Long Terminal Repeat) of RSV (Rous Sarcoma Virus).

As examples of other promoters whose use may be considered, mention should be made of:
the promoter of the IE gene of CMV (cytomegalovirus)
the MMTV (Mouse Mammary umor Virus) inducible promoters or metallothionine promoters.

The strength of the promoter which is used may be estimated in assays similar to those which are described in the examples which follow, for example by replacing the promoter under study in the vectors of these examples by the promoter contained in the LTR of RSV and by the evaluation of the intensity of expression of the marker obtained, an intensity which can then be compared with that obtained with the promoter of LTR of RSV.

The amount of vectors administered to the organism is advantageously chosen so as to overwhelm the immune system of the organism into which they are injected Advantageously, the route of adminstration selected in the framework of the present invention is the intravenous or intraarterial route.

Among the diseases affecting muscle cells mentioned above, mention may be made of genetic diseases such as muscular dystrophy.

Consequently, the nucleic acid inserted into the genome of the viral vector and the diffusion of which into the muscle mass is desired, comprises a nucleotide sequence coding for a polypeptide capable of treating the disease in question, and more particularly of playing the role in the muscle cell of the polypeptide normally present in a healthy cell, but the deficiency of which is due either to an abnormally low level or the complete failure of the production of this polypeptide, or to an error in its amino acid sequence which results from genetic anomalies in its coding nucleotide sequence.

Vectors according to the invention used to produce a medicine designed for the treatment of muscular dystrophy are more particularly characterized in that the nucleic acid insert is constituted by all or part of a healthy gene for dystrophin. The introduction of the entire gene for dystrophin or even of any part of this gene which codes for a polypeptide conserving an activity similar to that of the whole protein can be carried out in accordance with a method identical with that described hereafter for the introduction of the gene for beta-galactosidase.

As examples of diseases other than muscle diseases, susceptible to treatment in the framework of the present invention, mention may be made of the thromboses originating from infarctuses or also phlebites.

Vectors according to the invention used to produce a drug designed for the treatment of thromboses and for the prevention of infarcts and phlebites are more particularly characterized in that the nucleic acid insert comprises a nucleotide sequence coding for a thrombolytic substance. The latter sequence is advantageously preceded by a signal sequence which codes for a peptide signal which ensures the secretion of the thrombolytic substance outside the muscle cell.

The invention also relates to any recombinant vector characterized in that it is constituted of the defective genome of an adenovirus comprising, nonetheless; all of the essential sequences necessary for the encapsidation of this adenovirus, and into which is inserted a recombinant nucleic acid, the diffusion of which is desired in the muscle mass, this nucleic acid being placed under the control of a promoter capable of being recognized by the polymerases of the muscle cells, in particular by the strong promoter of the ElA early region of the genome of the adenoviruses.

A preferred recombinant vector of the invention is characterized in that this recombinant nucleic acid is constituted by all or part of the gene for dystrophin.

The invention also relates to pharmaceutical compositions consisting one or more recombinant vectors such as those described above, in combination with a pharmaceutically acceptable vehicle.

The subject of the invention is also a procedure for producing the recombinant vectors described above which comprises, after the construction stage itself of these vectors by the introduction of the nucleic acid insert into their genome, a transformation step of transformable cell lines of higher eukaryotes (particularly of human or animal origin), themselves carrying a distinct nucleotide sequence capable of complementing the part of the genome of the adenovirus essential for the replication thereof and which the above-mentioned vector lacks, the said distinct sequence being preferably incorporated into the genome of the cells of the said cell line.

As a preferred example of such cell lines, mention should be made of line 293, a human embryonic kidney line which contains, integrated into its genome, the first eleven percent of the lefthand end of the genome of an Ad5. This portion complements defective recombinant viruses which bear deletions in this region. Such a production procedure is more particularly described in the European patent application No. 0 185 573 of 20/11/85.

After transformation of these cell lines, the vectors which are thus multiplied are recovered and purified.

The present invention will be illustrated more particularly with the aid of the detailed description which follows of the construction of recombinant adenovirus vectors comprising the gene coding for beta-galactosidase, and of the properties of this adenovirus vector.

1. Construction of the recombinant adenovirus, Ad-RSV-beta-gal, by means of in vivo recombination.

This recombinant adenovirus was constructed by homologous recombination between a suitable plasmid and the genome of a type 5 (Ad5) adenovirus. In this construction, the gene for beta-galactosidase is placed under the control of the RSV (Rous Sarcoma Virus) promoter. The plasmid pAdRSV "Bêta " ontains the PvuII segment of the lefthand end of the Ad5 (segment situated between the positions 0 and 1.3 of the plasmid in FIG. 1) comprising the inverted terminal repeat, the origin of replication, encapsidation signals and the amplifier Ela. This fragment is followed by a nlslacZ gene (described in Bonnerot, C. et al., Proc. Nati. Acad. Sci. USA, 1987, 84, 6795–6799) which codes for beta-galactosidase, and by a fragment of the adenovirus Ad5 situated between the positions 9.4 and 17 of the plasmid of FIG. 1.

The values of the positions 1.3, 9.4 and 17 indicated above are units indicating the number of base pairs included within these fragments, one unit representing 360 base pairs.

The AdS sequence situated between the above-mentioned positions 9.4 and 17 allows recombination with the adenovirus dl324 treated by the restriction enzyme ClaI (corresponding to a deletion mutant E3; the deletion being made between the positions 78.4 and 84.3 of the genome of the adenovirus shown in FIG. 1), after transfection of 293 cells (human embryonic kidney cells transformed by the adenovirus and mentioned above) in order to generate the recombinant vector Ad-RSV-betagal. The nlslacZ gene is controlled by the RSV LTR promoter and possesses the polyadenylation signal of the SV40 virus. The recombinant virus thus obtained is incapable of replicating on account of the deletion of the E1 genes.

2. Study of the transfer of the gene to the organs of the mouse through the intermediary of the adenovirus.

Four day old Balb/C mice are given an intravenous injection of 20–40 microliters of highly purified recombinant adenovirus Ad-RSV-betagal ($10^9$ plaque-forming units: PFU/ml), the organs were excised 15 days after the injection and treated with 4% paraformaldehyde in a phosphate buffer for 30 minutes. After being rinsed, the organs were incubated overnight at 30° C. in a X-gal solution. The whole organs were then frozen and treated appropriately so that cryosections (10 micrometers thick) could be prepared and these sections were staned with the aid of hematoxylin and eosin.

The demonstration by means of histochemical staining in the manner indicated above of beta-galactosidase activity in the sections prepared indicates the presence of the gene inserted into the adenovirus vector. in the cells of the excised organs. The macroscopic examination of the heart as well as the skeletal muscles excised from these treated mice reveals the great efficiency with which this gene transfer was made after only one injection of the recombinant adenovirus. The significance of the choice of the intravenous route resides in the fact that the viral vector is not concentrated in any particular zone of the muscle tissue but, conversely, it is favourably distributed throughout the muscle mass. The histochemical staining leads to estimates that the number of transformed cells in some zones attains as much as 50% of the number of muscle cells present in this zone.

The expression of beta-galactosidase in the myocardium as well as in the skeletal muscles is perfectly stable. It was possible to observe positive stains 15, 33, 55, 66, 90, 127 and 150 days after the injection of the recombinant adenovirus. The expression of the gene seems to be constant as a function of time since the proportion of blue cells in the muscle tissues seem to be more or less the same from one month to the next.

The analysis of isolated muscle fibers reveals that a single fiber is likely to offer many "centers of expression".

Analyses by (Southern) immunoblot performed on the heart of a treated mouse have led to the demonstration of an intense and unique band at 35 kbp indicating that the viral DNA introduced into the muscle cells is essentially extra-chromosomal.

We claim:

1. A method for delivering to human and animal muscle cells a recombinant vector comprising a defective genome of an adenovirus, comprising all of the essential sequences necessary for the encapsidation of said adenovirus, and a nucleic acid sequence encoding a polypeptide sequence which nucleic acid sequence is inserted into a deleted EA and EB transactivator region of said recombinant vector said process comprising the step of:

(a) injecting intravenously or intraarterially said recombinant vector wherein said nucleic acid sequence is under the control of a promoter recognized by polymerases of said muscle cells wherein said recombinant vector is delivered to said human and animal muscle cells and wherein said polypeptide is expressed in said muscle cells.

2. The method according to claim 1, wherein said nucleic acid sequence encodes a polypeptide having thrombolytic properties.

3. The method according to claim 1, wherein said nucleic acid sequence encodes a polypeptide which is all or part of a dystrophin gene product.

4. The method according to claim 1, said nucleic acid sequence encodes a polypeptide which is a β-galactosidase gene product.

5. The method according to claim 1, wherein said promoter is a promoter contained in the Long Terminal Repeat of a Rous Sarcoma Virus.

6. The method according to claim 1, wherein said promoter is an adenoviral E1A early region promoter.

* * * * *